United States Patent
Hellström et al.

(10) Patent No.: US 6,348,447 B1
(45) Date of Patent: Feb. 19, 2002

(54) PHARMACEUTICAL COMPOSITION FOR THE TREATMENT OF FUNCTIONAL DYSPEPSIA AND/OR IRRITABLE BOWEL SYNDROME AND NEW USE OF SUBSTANCES THEREIN

(76) Inventors: Per Hellström, Svärdsjövägen 1, 16775 Bromma; Suad Efendic, Stjärnvägen 16B, 18134 Lidingö, both of (SE)

(*) Notice: Subject to any disclaimer, the term of this patent is extended or adjusted under 35 U.S.C. 154(b) by 0 days.

(21) Appl. No.: 09/445,571

(22) PCT Filed: Jun. 8, 1999

(86) PCT No.: PCT/SE99/00997

§ 371 Date: Feb. 3, 2000

§ 102(e) Date: Feb. 3, 2000

(87) PCT Pub. No.: WO99/64060

PCT Pub. Date: Dec. 16, 1999

(30) Foreign Application Priority Data

Jun. 11, 1998 (SE) ............................................... 9802080

(51) Int. Cl.$^7$ .............................................. A61K 38/00
(52) U.S. Cl. ............................ 514/12; 514/2; 530/300; 530/324; 530/325; 530/326; 530/327
(58) Field of Search ...................... 530/300, 324–327; 514/2, 12–14

(56) References Cited

FOREIGN PATENT DOCUMENTS

| WO | 97/01579 | 1/1997 |
| WO | 98/03547 | 1/1998 |

OTHER PUBLICATIONS

Drossman et al. 1992. Annals of Internal Medicine 116 (12 pt 1):1009–1016*
Habener et al. 1993. Endocrinology and Metabolism Clinics of North America 22(4):775–794.*
Nauck et al. 1993. J. Clinical Endocrinology and Metabolism 76(4):912–917.*
J. Behar et al., 1980. "Effect of cholecystokinin and the octapeptide of cholecystokinin on the feline sphincter of Oddi and gallbladder." J. Clin. Invest., 66:1231–1239.
G. Bertaccini et al., 1971. "Action of of caerulein on intestinal motility in man." Gastroenterology, 60:55–63.
Blackburn et al., 1980. "Effect of neurotensin on gastric function in man." Lancet, i:987–989.
Drossman et al., 1992. "The irritable bowel syndrome: Review and a graduated multicomponent treatment approach." Ann. Intern. Med. 116:1009–1016.
S. Efendic et al., 1978. "Effect of somatostatin on intestinal motility." Acta. Radiol. Diagn. 19:348–351.
J.F. Habener, 1993. "The incretin notion and its relevance to diabetes." Endocrinol. Metab. Clin. North Am. 22:775–794.
R.A. Liddle et al., 1986. "Regulation of gastric emptying in humans by cholecystokinin." J. Clin. Invest. 77:992–996.

J.A. Levant et al., 1974. "The effects of graded doses of C–terminal octapeptide of cholecystokinin on small intestinal transit time in man." Dig. Dis. 19:207–209.
B.M. Meyer et al., 1989. "Role of cholecystokinin in regulation of gastrointestinal motor functions." Lancet ii:12–15.
A.K. Mukhopadhyay et al., 1977. "Effect of cholecystokinin on myoelectric activity of small bowel of the dog." Am. J. Physiol. E44–E47.
M.A. Nauck et al., 1993. "Additive insulinotropic effects of exogenous synthetic human gastric inhibitory polypeptide and glucagon–like peptide–1–(7–36) amide concentrations." J. Clin. Endocrinol. Metab. 76:912–917.
H.S. Ormsbee et al., 1978. "Somatostatin inhibits motilin–induced interdigestive contractile activity in the dog." Dig. Dis. 23:781–788.
E. Sandberg et al., 1988. "Cholecystokinin–33 potentiates and vasoactive intestinal polypeptide inhibits gastric inhibitory polypeptide–induced insulin secretion in the perfused pancreas." Acta. Endocrinol. 117:545–551.
J.C. Schang et al., 1981, "Inhibition of canine interdigestive proximal gastric motility by cholecystokinin octapeptide." Am. J. Physiol. 240:G217–G220.
W.J. Snape et al., 1977. "Human colonic myoelectric activity in response to prostigmin and the gastrointestinal hormones." Dig. Dis. 22:881–887.
K. Thor et al., 1986. "Neurotensin increases colonic motility," Gastroenterology 90:27–31.
K. Thor et al., 1982. "(Gln$^4$)–neurotensin changes the motility pattern of the duodenum and proximal jejunum from a fasting–type to a fed–type," Gastroenterology 83–569–574.
T. Tolessa et al., 1998. "Inhibitory effect of glucagon–like peptide–1 on small bowel motility." J. Clin. Invest. 102:764–774.
T. Tolessa et al., 1998. "Glucagon–like peptie–1 retards gastric emptying and small bowel transit in the rat." Dig. Dis. Sci. 43:2284–2290.

(List continued on next page.)

Primary Examiner—Karen Cochrane Carlson
(74) Attorney, Agent, or Firm—McDermott, Will & Emery

(57) ABSTRACT

The invention relates to the new use of gastrointestinal peptide hormones selected from the class consisting of glucagon-like peptide-1 (GLP-1) and derivatives thereof having anti-secretory effects and smooth muscle relaxatory properties in the gastrointestinal tract for the manufacture of a pharmaceutical composition for the treatment of functional dyspepsia and/or irritable bowel syndrome. The invention also relates to a pharmaceutical composition comprising a combination of at least one member selected from said class consisting of GLP-1 and derivatives thereof with one or more other gastrointestinal peptide hormone(s) or derivative (s) thereof together with pharmacologically acceptable additives and to a method of treating functional dyspepsia or irritable bowel syndrome or both by administering an effective amount of at least one member of said class consisting of GLP-1 and derivatives thereof having effects and properties as mentioned above.

5 Claims, No Drawings

OTHER PUBLICATIONS

A. Wettergren et al., 1998. "Glucagon–like peptide–1 inhibits gastropancreatic function by inhibiting central parasympathetic outflow." Am. J. Physiol. 275:G984–G992.

W.M. Yau et al., 1993. "Modulation of cholinergic neurotransmitter release from myenteric plexus by somatostatin." Peptides 4:49–53.

* cited by examiner

PHARMACEUTICAL COMPOSITION FOR THE TREATMENT OF FUNCTIONAL DYSPEPSIA AND/OR IRRITABLE BOWEL SYNDROME AND NEW USE OF SUBSTANCES THEREIN

This application is a 371 of PCT/SE99/00997 filed Jun. 8, 1999 which claims priority to Swedish application 98 02080-3 filed Jun. 11, 1998.

The present invention relates to a new use of a gastrointestinal peptide hormone or a derivative thereof, to a pharmaceutical composition for the treatment of functional dyspepsia and/or irritable bowel syndrome, and to a method for such treatment.

Functional diseases are characterized by disordered function of the organ or organ system and no obvious structural pathology can be detected neither macroscopically nor microscopically. This should be differentiated from morphologic pathological diseases where the structure of the organ is changed from normality to abnormality. This type of disease can always be diagnosed either macro- or microscopically, and may be followed by functional aberration of the organ.

In the gastrointestinal tract the two most common functional disorders are functional dyspepsia and disordered gastrointestinal motility, commonly known as irritable bowel syndrome (IBS). These two terms are not exclusive determinants for separate disease entities, but instead the most common expressions for various overlapping symptoms emerging from the upper and lower gastrointestinal tract.

Abdominal pain or discomfort is remarkably common in the general population. The annual prevalence of recurrent abdominal pain or discomfort in Western countries is approximately 25%. If frequent heartburn with retrosternal burning pain or discomfort is also considered the prevalence approaches 40% (Locke et al, 1997; Agréus and Talley, 1997; Talley et al, 1992).

The term dyspepsia refers to chronic or recurrent pain or discomfort centered in the upper abdomen. The major organic diseases that cause dyspepsia are gastroduodenal ulcer, gastroesophageal reflux and gastric cancer. Up to 60% of patients with dyspepsia have no definite explanation for their symptoms and are classified as having functional dyspepsia. These patients may respond to reassurance and explanation of the background to their symptoms, and at times anti-secretory or motility regulatory pharmacotherapy. Even though the bacteria Helicobacter pylori may be encountered in patients with functional dyspepsia, it is yet not recommendable to pursue eradication therapy unless a peptic ulcer is found, and is often of limited value in relieving symptoms. In patients with persistent symptoms, other treatments that may be considered include behavioral therapy, psychotherapy, or antidepressant therapy, but these approaches are not of established value.

The management of dyspepsia represents a major issue in clinical practice; 2–5% of all general practice consultations are accounted for by dyspepsia. Yet, as no obvious cause for the disease is at hand, treatment strategies have to be empirical; either aiming at anti-secretory or motility regulatory therapeutic measures.

Among different treatment strategies available for functional dyspepsia these include: motility regulatory agents, antacids, $H_2$-receptor antagonists and, often prokinetics.

Gastrointestinal motility disorders are considered a common cause of functional dyspepsia. In cases of slow gastric emptying, motility stimulating agents, so-called prokinetics such as metoclopramide (Albibi et al, 1983) and cispride (Reboa et al, 1984; Delattre et al, 1985; Rösch, 1987; Abell et al, 1990), have been tried with reported symptomatic relief. In spite of this observation there is an undefined relationship between slow gastric emptying and symptoms and it is therefore unclear if the observed symptomatic relief depends on normalization of gastric emptying rate. Recent clinical trials with cisapride have disclosed symptomatic relief in 60–90% of the studied patients with dysmotility-like and gastroesophageal reflux-like dyspepsia, which should be compared to a 5–60% relief in placebo-treated groups (Talley 1991). Treatment with prokinetic drugs may thus be worthwhile, but does not resolve the problem.

Antacids have generally been considered as potentially effective in treatment of dyspeptic symptoms. No reliable data are available on their efficacy in functional dyspepsia (Talley, 1991), and antacids may rather be used as an on-demand treatment than continuous medication against functional dyspepsia.

$H_2$-receptor antagonists, such as cimetidine and ranitidine, have been studied in the treatment of functional dyspepsia. About half of the reported studies show paucity of therapeutic response, whereas others have found statistic evidence for a therapeutic response to $H_2$-receptor antagonist therapy (Talley, 1991). Mainly, patients with ulcer-like symptoms in the form of burning epigastric pain, may gain some symptomatic relief (Delattre et al, 1985) with $H_2$-receptor antagonists. In addition to this, it is an every day experience that patients may benefit from an even more profound anti-secretory treatment by the use of a proton pump inhibitor such as omeprazole, lansoprazole or pantoprazole.

Thus, some symptomatic relief may be achieved with agents that inhibit gastric acid secretion.

IBS is common and involves about 1–2% of the population and accounts for up to one third of doctor's visits in general practice. The disease seems to be life-long with continuous relapsing activity, but it has not yet been studied how the disease affects the subject over a life span. No effective treatment is yet available. One major obstacle for the development of an effective drug is the fact that no reliable diagnostic hallmark of the disease is at hand, and for diagnostic purposes the doctor has to rely on the patient's case history and subjective reports, mainly as pain episodes and variable bowel habits.

During symptomatic periods a pattern of hypermotility, consisting of high-amplitude pressure waves are ten times as common in pain-dominant IBS than in normal subjects, whereas patients with the diarrhea-predominant disorder have normal or lower than normal pressure waves. These observations fit with basic data from recordings of colonic motility of normal subjects and patients with constipation or diarrhea. Such studies have demonstrated that the predominant form of motor activity from the colon consists of segmental contractions, which impede the propulsion of stool and promote mixing and absorption of water. These segmental contractions appear for more than 90% of the recorded time. Augmentation of segmental contractions produces constipation and inhibition of segmentation motor activity produces diarrhea. Studies indicate that contractions over a long segment of the colon may be accompanied by abdominal pain, analogous to diffuse esophageal spasm, the nutcracker syndrome of the esophagus and chest pain. Such high-amplitude contractions over long segments of the gut are often recorded in patients with IBS under episodes of crampy abdominal pain, i.e. the "gut-cracker syndrome". Hypermotility of the small intestine also has been found in association with pain. Anecdotal evidence speak in favor of spasmodic cramping as the major source of symptoms in irritable bowel syndrome. Thus, regarding the pathophysiology of irritable bowel syndrome, disordered gastrointestinal motility or disturbances in the sensory system, or both, are suggested to be most important factors. However, there are many reports demonstrating disturbed small intestinal motility in patients with IBS in terms of the migrating motor complex activity. In the fasted state this activity includes phase I, displaying quiescence with no motor activity, phase II with sporadic contractions that become more intense over time and precede the characteristic phase III with high amplitude contractions to a level of about 40–50 mm Hg. In irritable bowel syndrome, increased phase II contraction frequency, increased contraction amplitude, and increased clustered contractions have been described (Kellow et al, 1987; Kellow et al, 1990; Lind, 1991; Kellow et al, 1992; Schmidt et al, 1996; Evans et al, 1996; Small et al, 1997). Radiologic studies demonstrate small bowel motor hyperactivity under stress and support the contention that IBS can involve also other parts of the gastrointestinal tract than the colon. Reports also exist which fail to detect any disturbance in intestinal motility in patients with IBS (Gorard et al, 1994).

A number of studies point in favor of sensory disturbances, such as mechanoreceptor hypersensitivity (Kellow et al, 1988; Evans et al, 1996) and an increased awareness of intestinal distension and contractions (Kellow et al, 1992).

According to the present invention it has now surprisingly been found that the disturbances characterizing functional dyspepsia and/or IBS can be normalized by the administration of certain substances which combine anti-secretory effects with smooth muscle relaxatory properties (i.e. motility inhibiting rather than motility stimulating effects).

A great number of peptides have been disclosed in the gastrointestinal tract during the last 25 years. Some of these peptides are considered endocrine in their action as they are located within mucosal cells of the "open type" reaching the lumen with their apical surface and the wide-based bottom towards the blood vessels permitting a release of peptides to the circulation. The peptides are regularly stored within dense large granulae, which can be depleted in exchange for ionized calcium. The peptides released to the blood stream may act as hormones at sites distant from their release or locally as paracrine substances. Their actions may be involved in the control of different gastrointestinal functions such as absorption, secretion, blood flow and motility.

A number of gastrointestinal peptide hormones have both anti-secretory effects and smooth muscle relaxatory properties in the gastrointestinal tract. A especially potent and thereby interesting peptide hormone of this category is glucagon-like peptide-1 (GLP-1).

Glucagon-like peptide-1 (GLP-1) is a newly discovered peptide considered an incretin as it enhances food-stimulated insulin secretion (Habener 1994). GLP-1 inhibits gastric acid secretion by 43% and slows gastric emptying by 50% in man (Wettergren et al, 1993; Gutniak et al, 1996), along with an inhibition of pancreatic secretion by about 45% (Wettergren et al, 1993).

The present invention is based on the recent findings by the present inventors that GLP-1 has a profound inhibitory action not only on gastric emptying, but also on small intestinal motility in the rat. Data indicate that the effect of GLP-1 on motility is not mediated by either insulin or somatostatin, but stands alone as a probably direct effect on intestinal smooth muscle. Additionally, the inventors have found that GLP-1 decreases small bowel motility in humans with IBS.

On basis thereof, according to a first aspect of the present invention, there is provided the use of a gastrointestinal peptide hormone selected from the class consisting of glucagon-like peptide-1 and derivatives thereof having anti-secretory effects and smooth muscle relaxatory properties in the gastrointestinal tract for the manufacture of a pharmaceutical composition for the treatment of functional dyspepsia and/or irritable bowel syndrome.

Further according to the invention it may be preferable to combine said GLP-1 or derivatives thereof with one or more other gastrointestinal peptide hormone(s) or derivative(s) thereof in the pharmaceutical composition in order to achieve complementary effects. In a particularly preferred embodiment the gastrointestinal peptide somatostatin is combined with GLP-1 in the pharmaceutical composition.

According to another aspect of the present invention there is provided a pharmaceutical composition for the treatment of functional dyspepsia and/or irritable bowel syndrome which composition is characterized in that it comprises a combination of at least one member of the group consisting of GLP-1 and derivatives thereof having anti-secretory effects and smooth muscle relaxatory properties in the gastrointestinal tract with one or more other gastrointestinal hormone(s) and derivative(s) thereof having such effects and properties together with pharmacologically acceptable additives.

A preferred embodiment of the pharmaceutical composition according to the invention is characterized in that the composition comprises GLP-1 in combination with somatostatin.

The pharmaceutical composition according to the invention may take various forms, such as, for instance, powders, granules, tablets, sugar-coated tablets, capsules, syrups, suppositories, injectable solutions, preparations for inhalation including nasal administration, for buccal (lozenges), percutaneous (plasters) or subcutaneous administration comprising the active ingredient or ingredients in admixture with components necessary for the formulation of the compositions, such as pharmacologically acceptable additives (e.g. carrier, excipient or diluent).

According to a further aspect of the invention there is provided a method for the treatment of functional dyspepsia or irritable bowel syndrome or both in a human patient suffering therefrom, which method comprises administering to said patient an effective amount of at least one member selected from the group consisting of GLP-1 and derivatives thereof having anti-secretory effects and smooth muscle relaxatory properties in the gastrointestinal tract.

According to a preferred embodiment of the method according to the invention GLP-1 is administered in combination with somatostatin. In this case the two substances may be administered in form of separate formulations or in admixture in one single formulation.

The term "an effective amount" as used in the description and the claims is intended to designate a dose which causes a marked relief of the symptoms.

As is generally perceived by the man of ordinary skill in the art the dosage will vary depending on the administration routes, symptoms and body weight of the patient but also depending on GLP-1 or derivative thereof being administered.

In case of injections the dose of GLP-1 is generally within the range of 40–200 pmol/kg body weight/h, preferably 70–150 pmol/kg body weight/h. In combination with somatostatin, a dose of 2–15 μg/kg body weight/h, preferably 4–7 μg/kg body weight/h of somatostatin should be used.

The administration frequency can suitable be selected within the range from once to four times a day.

The invention will now be further illustrated by means of an Example, which illustrates the best mode contemplated at present for carrying out the invention.

EXAMPLE

Decrease of Small Bowel Motility in Humans with IBS

Experiments were carried out in 12 subjects fulfilling the Rome-criteria for IBS. In the fasted subjects a small bowel manometry tube was passed through the nose and located in antroduodenal region under fluoroscopy. Then, small bowel manometry was recorded for 8 hours in the fasted state, and for an additional 40 min after a meal (320 kcal). During the first 4-hour period of the recording saline was administered intravenously. During the second 4-hour period GLP-1 was given intravenously either at a dose of 1.2 pmol/kg/min (72 pmol/kg/h) (n=6) or 2.5 pmol/kg/min (150 pmol/kg/h) (n=6) with the infusion continued over the 40-minute meal period. GLP-1 was administered as an intravenous infusion at a dose of 1.2 or 2.5 pmol/kg/min. The compound was diluted from a stock solution of GLP-1 (Polypeptide, Wolfenbüttel, Hannover, Germany) 100 nmol/ml prepared according to general guidelines with sterilization filtration and endotoxin test, and divided in 10 ml ampoules.

For each patient the solution for infusion was constituted according to body weight. The dose to be given was multiplied by body weight, resulting in an individual dosing, expressed as pmol/min. The calculated total dose (according to extrapolated 250 ml infusion time) was taken from the stock solution and diluted in 250 ml infusion volume of saline (Natriumklorid 9 mg/ml, Pharmacia & Upjohn, Stockholm, Sweden). The infusion was then given at a rate of 1 ml/min with a constant infusion pump (Volumetric infusion pump, model 960, Imed, Oxon, UK) over 4 hours (240 min).

The overall result showed that GLP-1 was able to reduce the motor activity in IBS patients. However, within 14.2±3.8 min after onset of GLP-1 infusion at 1.2 pmol/kg/min, and within 12.0±2.7 min after onset of GLP-1 infusion at 2.5 pmol/kg/min, an MMC was started in the duodenum in four out of six patients in each group. As this premature MMC cycle was considered to be due to an immediate effect of GLP-1 during a build-up of a steady state concentration in the circulation, an adjusted MMC prevalence during GLP-1 infusion was calculated by subtracting the premature MMC at onset from the remaining MMC observed during infusion of GLP-1.

In detail, the following results were obtained from the motility recordings (reference point: angle of Treitz; values are mean ±SEM of n=6 in each group; statistical evaluation by the non-parametric Wilcoxon signed-rank test):

| Dose | Saline | GLP-1 1.2 pmol/ kg/min | Saline | GLP-1 2.5 pmol/ kg/min |
| --- | --- | --- | --- | --- |
| Contraction frequency (#/min) | 1.7 ± 0.2 | 1.7 ± 0.4 | 2.0 ± 0.3 | 0.9 ± 0.2 (p < 0.031) |
| Contraction amplitude (mm Hg) | 26.7 ± 2.7 | 24.7 ± 1.6 | 30.7 ± 2.8 | 23.6 ± 2.5 (p < 0.062) |
| Contraction area (mm Hg*s) | 39.1 ± 5.0 | 33.4 ± 3.2 | 47.9 ± 5.9 | 30.5 ± 5.3 |
| Motility index Ln (Sum (mm Hg*s)/min) | 4.9 ± 0.2 | 4.7 ± 0.3 | 5.3 ± 0.2 | 3.8 ± 0.8 |
| Adjusted MMC (#/4 h) | 1.3 ± 0.5 | 0.0 ± 0.0 (p < 0.062) | 1.0 ± 0.5 | 0.2 ± 0.2 (p < 0.062) |

# = number; MMC = migrating motor complex

In summary, in the fasted state GLP-1 exhibits a dose-dependent reduction of motor activity in the small bowel in patients suffering from irritable bowel syndrome. In conclusion this implies that GLP-1 may be used as a therapeutic agent for symptomatic relief in cases with functional dyspepsia and/or irritable bowel syndrome, both of which characterized by irregular motor activity in the gut.

REFERENCES

Abell T L, Camilleri M, DiMagno E P, Hench V S, Zinsmeister A R, Malagelada J R. Long-term efficacy of oral cisapride in symptomatic upper gut dysmotility. Dig Dis Sci 1990; 36: 616–620.

Agréus L, Talley N. Challenges in managing dyspepsia in general practice. B M J 1997; 315: 1284–1288.

Albibi R, McCallum R W. Metoclopramide: pharmacology and clinical application. Ann Intern Med 1983; 98; 86–95.

Delattre M, Malesky M, Prinzie A. Symptomatic treatment of non-ulcer dyspepsia with cimetidine. Curr Ther Res 1985; 37: 980–991.

Evans P R, Bennett E J, Bak Y -T, Tennant C C, Kellow J E. Jejunal sensorimotor dysfunction in irritable bowel syndrome: Clinical and psychosocial features. Gastroenterology 1996; 110: 393–404.

Gorard D A, Libby G W, Farthing M J G. 5-Hydroxytryptamine and human small intestinal motility: effect of inhibiting 5-hydroxytryptamine uptake. Gut 1994; 35: 496–500.

Gutniak M K, Junttii-Berggren L, Hellström P M, Guenifi A, Holst J J, Efendic S. GLP-1 (glucagon-like peptide-1) enhances the insulinotropic effect of glibenclamide in NIDDM patients and in the perfused rat pancreas. Diabetes Care 1996; 19: 857–863.

Habener J F. The incretin notion and its relevance to diabetes. Endocrinol Metab Clin North Am 1994; 25: 25–31.

Kellow J E, Eckersley G M, Jones M. Enteric and central contributions to intestinal dysmotility in irritable bowel syndrome. Dig Dis Sci 1992; 37: 168–174.

Kellow J E, Gill R C, Wingate D L. Prolonged ambulant recordings of small bowel motility demonstrate abnormalities in irritable bowel syndrome. Gastroenterology 1990; 98: 1208–1218.

Kellow J E, Phillips S F. Altered small bowel motility in irritable bowel syndrome is correlated with symptoms. Gastroenterology 1987; 92: 1885–1893.

Kellow J E, Phillips S F, Miller L J, Zinsmeister A R. Dysmotility of the small intestine in irritable bowel syndrome. Gut 1988; 29: 1236–1243.

Lind C D. Motility disorders in the irritable bowel syndrome. Gastroenterol Clin North Am 1991; 20: 279–295.

Locke G R, Talley N J, Fett S, Zinsmeister A R, Melton L J III. Prevalence and clinical spectrum of gastroesophageal reflux in the community. Gastroenterology 1997; 112: 1448–1456.

Reboa G, Arnulfo G, DiSomma C et al. Prokinetic effect of cisapride on normal and reduced antroduodenal motility and reflexes. Curr Ther Res 1984; 36: 18–23.

Rösch W. Cisapride in non-ulcer dyspepsia. Scand J Gastroenterol 1987; 22: 161–164.

Schmidt T, Hackelsberger N, Widmer R, Meisel C, Pfeiffer A, Kaess H. Ambulatory 24-hour jejunal motility in diarrheapredominant irritable bowel syndrome. Scand J Gastroenterol 1996; 31: 581–589.

Small P K, Loudon M A, Hau C M, Noor N, Cambell F C. Large-scale ambulatory study of postprandial jejunal motility in irritable bowel syndrome. Scand J Gastroenterol 1997; 32: 39–47.

Talley N J. Drug treatment of functional dyspepsia. Scand J Gastroenterol 1991; 26(suppl 182): 47–60.

Talley N J, Zinsmeister A R, Schleck C D, Melton III L J. Dyspepsia and dyspepsia subgroups: a population-based study. Gastroenterology 1992; 102: 1259–1268.

Wettergren A, Schjoldager B, Mortensen P E, Myhre J, Christiansen J, Holst J J. Truncated GLP-1 (proglucagon 78–107-amide) inhibits gastric and pancreatic functions in man. Dig Dis Sci 1993; 38: 665–673.

What is claimed is:

1. A pharmaceutical composition for the treatment of functional dyspepsia and/or irritable bowel syndrome characterized in that it comprises a combination of at least one member selected from the group consisting of GLP-1 and derivatives thereof having anti-secretory effects and smooth muscle relaxatory properties in the gastrointestinal tract with somatostatin together with pharmacologically acceptable additives.

2. Pharmaceutical composition according to claim 1, characterized in that it comprises somatostatin in combination with GLP-1.

3. Method for the treatment of functional dyspepsia or irritable bowel syndrome or both in a human patient suffering therefrom which method comprises administering to said patient an effective amount of at least one member of the group consisting of GLP-1 and derivatives thereof having anti-secretory effects and smooth muscle relaxatory properties in the gastrointestinal tract.

4. Method according to claim 3, wherein GLP-1 is administered in combination with somatostatin.

5. A method of treating functional dyspepsia and/or irritable bowel syndrome, the method comprising administering to a patient in need of such treatment a composition comprising a combination of at least one member selected from the group consisting of GLP-1 and derivatives thereof having anti-secretory effects and smooth muscle relaxatory properties in the gastrointestinal tract, one or two more other gastrointestinal peptide hormone(s) or derivative(s) thereof having anti-secretory and smooth muscle relaxatory properties, and one or more pharmaceutically acceptable additives.

* * * * *